United States Patent [19]
Owens

[11] 3,947,897
[45] Apr. 6, 1976

[54] APPARATUS FOR CONNECTING A PROSTHESIS TO A BONE

[76] Inventor: Lester J. Owens, 3075 Saunders Place, Titusville, Fla. 32780

[22] Filed: Mar. 17, 1975

[21] Appl. No.: 559,108

[52] U.S. Cl. .................................. 3/2; 3/1; 3/1.9; 3/12; 3/18
[51] Int. Cl.² ..... A61F 1/08; A61F 1/06; A61F 1/00
[58] Field of Search .................. 3/1, 1.9–1.911, 3/2, 12, 12.1, 17–19, 21

[56] References Cited
UNITED STATES PATENTS

| | | | |
|---|---|---|---|
| 2,578,019 | 12/1951 | Ryan | 3/19 |
| 2,786,383 | 3/1957 | Bachman | 85/5 |

FOREIGN PATENTS OR APPLICATIONS

| | | | |
|---|---|---|---|
| 1,961,531 | 9/1970 | Germany | 3/1 |
| 2,114,323 | 10/1971 | Germany | 3/1 |

OTHER PUBLICATIONS
"A Permanently Attached Artificial Limb," by C. W. Hall et al., Transactions Amer. Society Artificial Internal Organs, Vol. XIII, 1967, pp. 329–331.

*Primary Examiner*—Ronald L. Frinks
*Attorney, Agent, or Firm*—James O. Harrell; John R. Manning

[57] ABSTRACT

An apparatus for connecting a prosthesis to a bone of a stump of an amputated limb such as the arm or leg of a person. The apparatus includes a tubular female socket adapted to be inserted within an intermedullary cavity of the bone. The tubular socket has an open lower end with a sleeve of bio-compatible material permitting access through the skin of the amputee's stump. The prosthesis has a contoured support for receiving the stump of the amputee. A quick disconnecting lock pin is carried adjacent the center of the contoured support. The lock pin is adapted to be received within the female socket for securing the prosthesis to the tubular female socket carried within the bone. The mounting for the lock pin is adjustable so that the degree of support provided through the bone as compared to the degree of support provided through the flesh of the stump engaging the wall of the prosthesis can be varied.

9 Claims, 4 Drawing Figures

APPARATUS FOR CONNECTING A PROSTHESIS TO A BONE

ORIGIN OF THE INVENTION

The invention described herein was made by an employee of the United States Government and may be manufactured and used by or for the Government for governmental purposes without the payment of any royalties thereon or therefor.

BACKGROUND OF THE INVENTION

This invention relates generally to an apparatus for connecting a prosthesis to an amputated limb and more particularly to an apparatus for attaching a prosthesis to the bone carried within the remaining stump of an amputated limb.

Heretofore, the most common way of attaching prosthesis to the stump of an amputated limb is by means of strap and harnesses that engage the stump of the limb. One problem encountered with such devices is that often there is not a tight, non-slipping connection between the prosthesis and the stump. Another problem encountered with mounting prosthesis to the stump of a limb by use of straps is that all of the supporting pressure, for example, when the prosthesis is an artificial leg, is transferred through the flesh of the stump. Oftentimes, such a mounting proves to be very uncomfortable to the wearer. Still another problem encountered by such devices for connecting artificial limbs to stumps of amputated limbs is the time required in securing the prosthesis to the stump.

SUMMARY OF THE INVENTION

The invention comprises a tubular female socket adapted to be inserted within an intermedullary cavity of the bone located within the stump of an amputated limb. The stump could be the stump of any amputated limb such as the leg or the arm. The medullary canal of the bone is cleaned out for the insertion of the female socket and the lower end of the bone is trimmed so that such will fit flush against a shoulder carried on the female socket. Bonding material is provided for attaching the female socket to the inner wall of the bone. The sleeve has a bio-compatible material encircling the lower end thereof so as to permit the skin to heal closely therearound. The prosthesis can be constructed of any suitable material such as structural plastic and has a socket for accommodating the stump. A quick disconnecting lock pin is mounted within a central portion of the socket. The lock pin is adapted to be inserted into an open end of the tubular female socket for connecting the prosthesis to the amputee's stump. The mounting for the lock pin includes an inner tubular sleeve positioned concentrically with an outer tubular sleeve. Positioned between the inner tubular sleeve and the outer tubular sleeve is a resilient material which acts as a shock absorber so as to minimize the shocks imparted to the bone through the connecting device. When the device is used as an upper leg attachment for a prosthesis, a yoke can be applied to the connecting device for transferring forces directly from the bone to other implements such as knee joints and lower artificial limbs.

Accordingly, it is an important object of the present invention to provide a new and novel connecting device for a prosthesis.

Another important object of the present device is to provide a quick connecting and disconnecting device for a prosthesis for enabling the prosthesis to be readily mounted to and removed from the stump of an amputated limb.

Still another important object of the present invention is to provide a connecting device which enables attaching directly to a bone for supporting a prosthesis.

These and other objects and advantages of the invention will become apparent upon reference to the following specification, attendant claims and drawings.

DESCRIPTION OF THE PREFERRED EMBODIMENT

Figure 1:
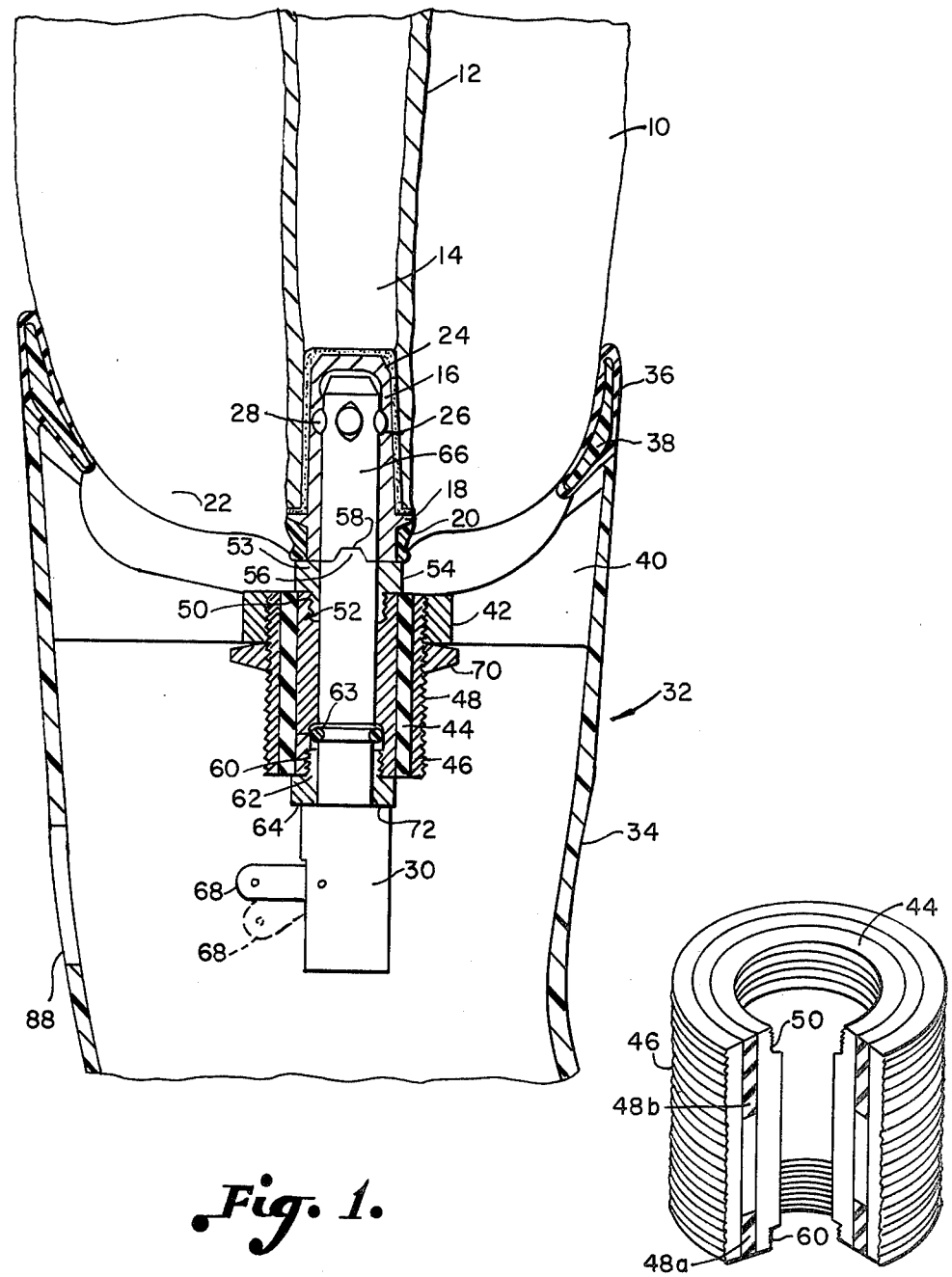
FIG. 1 is a cross-sectional view of a prosthesis and connecting device constructed in accordance with the present invention coupled to the stump of an amputated upper arm.

Referring in more detail to FIG. 1 of the drawings there is illustrated a stump 10 of an amputated limb such as the upper arm showing in cross section a portion of the bone 12 remaining in the stump. Marrow 14 carried in the lower end of the medullary canal is removed so as to accommodate a tubular female socket 16 which is constructed of any suitable material such as stainless steel. The socket 16 is inserted within the medullary canal into the lower end of the bone 12 which has been previously trimmed so that the bone 12 abuts against an outwardly extending shoulder 18 carried adjacent the lower end of the socket 16. A sleeve 20 of the bio-compatible material encircles the lower end of the female socket so as to provide a compatible innerface between the implanted socket 16 and the skin line 22 which heals therearound. One suitable material that is compatible with the flesh is vitreous carbon. The tubular female socket 16 is secured to the inner surface of the bone 12 by means of any suitable bonding material, such as methylmethacrylate. Normally, the outer surface of the sleeve is grooved or knurled so as to enable the bonding material to produce a good interference bond between the bone 12 and the socket 16. In order to minimize the stress between the socket 16 and the bone 12, the upper end of the socket such as at 24 tapers inwardly. The purpose of this inwardly tapering surface 24 adjacent the top of the socket 16 is to minimize stress concentration that may be incurred when the prosthesis is attached thereto. This inwardly tapering surface 24 may be curved slightly to form a portion of a three-dimensional ogive to match the curvature of the inner surface of the bone under maximum bending.

The tubular sleeve 16 has an annular groove 26 provided adjacent the upper end thereof for receiving balls 28 carried within a lock pin 30 for securing a prosthesis generally designated by the reference character 32 to the stump 10.

The prosthesis may be constructed of any suitable, conventional material and in one particular embodiment, it has an outer wall 34 constructed of structural plastic, or a soft skin-like material. A circular pressure contact pad 36 is carried adjacent the upper end of the prosthesis for engaging the flesh of the stump. Foam plastic 38 is carried between the pressure contact pad 36 and the structural wall 34 of the prosthesis. The foam plastic pad 38 with the pressure contact pad mounted thereon defines a socket which has a contour that conforms to the lower end of the stump 10. Such is fitted in the same manner as conventional prosthesis presently being utilized.

Positioned below the foam plastic 38 are four circumferentially spaced web members 40 which extend inwardly to the center axis of the prosthesis. The web members 40 are constructed of moldable plastic material and have a stainless steel ring 42 adhered thereto by any suitable means such as adhesive or such could be molded integral with the plastic webs 40. The ring 42 has internal threads.

Figure 2:
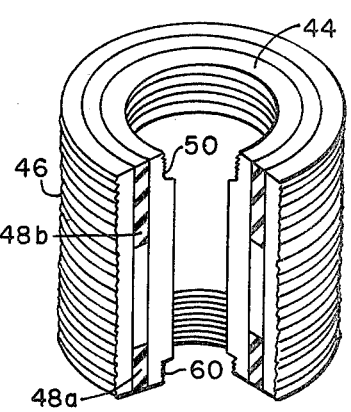
FIG. 2 is a cross-sectional view of a portion of a modified form of the connecting device.

The resilient mounting for the lock pin 30 includes an inner tubular sleeve 44, outer sleeve 46 and resilient material 48. The inner tubular sleeve 44 has internal threads adjacent the top and bottom thereof. The outer sleeve 46 is concentrically carried on the inner tubular sleeve 44 with resilient material 48 located between the inner and outer sleeves 44 and 46 respectively. The resilient material may be any suitable material such as silicone rubber manufactured by Dow Corning Corporation under Model No. 93-0372. The resilient material 48 acts as a shock absorbing device for the prosthesis. In one particular application, instead of filling the entire void between the inner sleeve 44 and the outer sleeve 46 with the resilient material 48, two spaced resilient rings, such as shown in FIG. 2 at 48a and 48b, are provided adjacent the bottom and top of the space between the inner sleeve 44 and the outer sleeve 46. Such enables the coupling to flex more than if the entire void were filled with the resilient material.

The inner sleeve 44 has a recessed threaded portion 50 adjacent the top for receiving a shank portion 52 of a bolt 53 which has an enlarged head 54. A bore extends through the bolt 53 in alignment with the bore extending through the inner sleeve 44. A protrusion 56 is carried on the upper surface of the enlarged head 54 for meshing with a recessed seat 58 carried in the bottom wall of the tubular socket 16. Such is to prevent the bolt from rotating relative to the sleeve 16. Another recessed threaded portion 60 is provided in the bottom of the inner sleeve 44 for accommodating another tubular bolt 62 which has an enlarged head 64 which can be adjusted relative to the bottom surface of the inner sleeve.

Any play or looseness of the lock pin 30 in the tubular socket 16 may be eliminated by rotating the tubular bolt 62. The enlarged head 64 of the tubular bolt 62 abuts against shoulder 72 carried on the bottom of the lock pin 30. As tubular bolt 62 is rotated, the enlarged head 64 engages shoulder 72 to move lock pin 30 slightly, thereby causing receiving balls 28 to be forced tightly into the lower portion of the annular groove 26. A coiled spring (not shown) may also be positioned around the shank of the lock pin 30 between shoulder 72 and the head 64 to take up any play or looseness of the balls 28 fitting in the groove 26.

The quick disconnecting lock pin 30 may be any suitable lock pin that has retractable balls 28 for locking a shank portion 66 within the socket 16. One suitable lock pin is disclosed in U.S. Pat. No. 2,786,383 granted to E. Bachman on Mar. 26, 1957. The details of the interior of the lock pin are not disclosed since such are conventional. The balls 28 are manipulated by a lever 68 extending out of a slot provided in the lower end of the lock pin. The stem portion 66 of the lock pin is coaxially disposed and slideably within the tubular socket 16, the inner sleeve 44 and the bores extending through the bolts 62 and 54.

It is noted that the outer sleeve 48 is threaded within the circular ring 42 for securing the coupling member within the prosthesis 32. A lock nut 70 is threaded on the outer sleeve 46 for preventing rotation of the coupling device relative to the ring 42.

In order to remove the prosthesis from the stump 10, it is only necessary to move the lever 68 from the full line position to the phantom line position. Such causes the balls 28 carried in the upper end of the lock pin to be retracted and disengage from the annular groove 26.

Figures 3, 4:
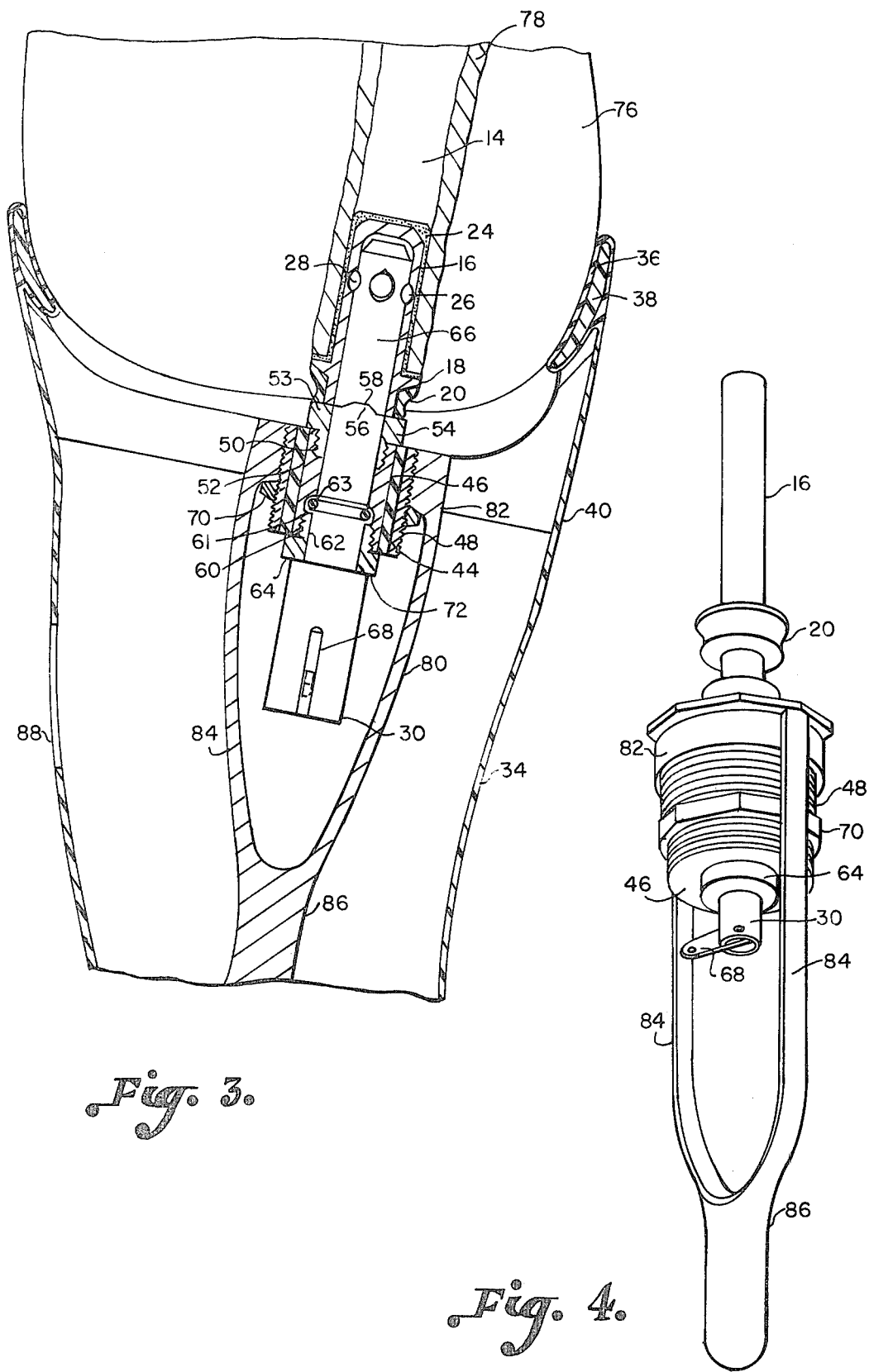
FIG. 3 is a cross-sectional view illustrating a connecting device and prosthesis constructed in accordance with the present invention coupled to the stump of an amputated upper leg.
FIG. 4 is an enlarged perspective view of the connecting device shown in FIG. 3.

FIG. 3 illustrates a prosthesis provided for attachment to an upper leg 76. The bone 78 of the upper leg is drilled out in the same manner as shown in FIG. 1 for receiving the socket 16.

Since the coupling device of FIG. 3 is identical to the coupling device of FIG. 1 with the exception that a yoke 80 is threaded on the outer sleeve 46 instead of the ring 42, like reference characters will be utilized for the corresponding and identical parts. The yoke 80 includes a circular ring 82 adjacent an upper portion which is molded into the webs 40 similar to the circular ring 42 of the prosthesis for the arm attachments or attached by any suitable means. Extending downwardly from the ring 82 are a pair of opposed arms 84 which are provided for failing if the force exerted through the bone to an attachment carried on the lower end of the prosthesis is too great. A primary circular support column 86 is integral with the bottom of the opposed arms 84 for providing means for attaching the yoke to a knee joint or the like carried below the prosthesis.

It has been proposed that the more load transferred through the bone, for example, in the upper leg rather than through the flesh in the stump, the more suitable the prosthesis is for use by the amputee. The amount of load transferred through the bone 78 can be varied by rotating the inner and outer sleeves 44 and 46 within the ring portion 82 of the yoke.

It is, of course, understood that the inner sleeve 44 and the outer sleeve 46 are adhered to each other by means of the resilient material 48 carried therebetween. In addition to the resilient material 48 absorbing shock, it also provides controlled failure device to prevent too great a force from being applied to the bone 78 by means of the prosthesis.

Since the compressive and frictional forces between the pads 36 of the prosthesis and the skin of the stump can be varied by rotating the outer sleeve 46 within the ring 82 of yoke 80, the amputee can readily adjust such pressure until it meets his desired comfort. A similar adjustment can be made with the arm prosthesis by rotating outer sleeve 46 within the threaded ring 42. The lock nut 70 serves to hold the outer sleeve 46 in the adjusted position.

An access window 88 is provided in the side of the prosthesis for enabling access to the lever 68 of the lock pin. An "O" ring 63 is carried within a groove 61 provided in the inner wall of the inner member 44. The purpose of the O ring is to provide a seal between the lock pin and the inner sleeve 44. It is also to be understood that a slidable or push-button type actuator may be employed in place of lever 68 to release the lock pin 30. This actuator could be located adjacent the outer wall 34 and the amputee would merely need to push or squeeze the outer surface of the prosthesis in order to release the same from his stump.

While a preferred embodiment of the invention has been described using specific terms, such description is for illustrative purposes only, and it is to be understood that changes and variations may be made without departing from the spirit or scope of the following claims.

What is claimed is:

1. An apparatus for connecting a prosthesis to a bone of a stump of an amputated limb comprising:
   a. a tubular female socket adapted to be inserted within an intermedullary cavity of the bone,
   b. said tubular female socket having an open lower end,
   c. a sleeve of bio-compatible material encircling said lower end of said female socket,
   d. said prosthesis having a contoured support for receiving said stump,
   e. a resilient mounting means carried adjacent the center of said contoured support, and
   f. a quick disconnecting lock pin supported by said resilient mounting means and adapted to be inserted in said open lower end of said tubular female socket for connecting said prosthesis to said tubular female socket and said stump.

2. The apparatus as set forth in claim 1 wherein:
   a. said bio-compatible material is vitreous carbon.

3. The apparatus as set forth in claim 1 wherein:
   a. said tubular female socket has an upper end with an inwardly tapering radius towards said upper end for minimizing stress concentrations between said tubular female socket and said bone.

4. The apparatus as set forth in claim 1 wherein said resilient mounting means includes:
   a. an outer sleeve having external threads thereon,
   b. a yoke,
   c. a circular collar carried by an upper end of said yoke having internal threads thereon,
   d. said circular collar being threaded on said external threads of said outer sleeve,
   e. means carried on an opposite end of said yoke from said collar for being coupled to other implements so as to transfer forces and loads through said coupling to the bone in said stump of the amputated limb.

5. The apparatus as set forth in claim 1, wherein said resilient mounting means includes:
   a. a ring carried on said contoured support of said prosthesis,
   b. said ring having internal threads thereon,
   c. an outer tubular sleeve having external threads mating with said internal threads of said ring,
   d. an inner tubular sleeve slidably receiving said quick disconnecting lock pin, and
   e. resilient material carried between said inner and outer sleeves.

6. The apparatus as set forth in claim 5, wherein said resilient material comprises:
   a. a pair of spaced resilient rings carried between said inner and outer sleeves.

7. The apparatus as set forth in claim 5 further including:
   a. a lock nut threaded on said outer tubular sleeve,
   b. whereby when said outer tubular sleeve is rotated in said ring to adjust the compressive force between said contoured support and said stump, said lock nut will serve to lock the prosthesis in the adjusted position desired by the amputee.

8. The apparatus as set forth in claim 1 further comprising:
   a. an annular groove carried in said tubular female socket,
   b. said quick disconnecting lock pin having selectively retractable balls carried thereon for seating in said annular groove so as to lock said lock pin and prosthesis to said tubular female socket.

9. The apparatus as set forth in claim 8, further comprising:
   a. an inner tubular sleeve slidably receiving said quick disconnecting lock pin and having internal threads thereon,
   b. a first tubular bolt having an enlarged head and a shank portion threaded in a lower end of said inner tubular sleeve,
   c. said quick disconnecting lock pin having a shoulder abutting against said enlarged head of said first tubular bolt,
   whereby by rotating said first tubular bolt within said inner sleeve, the looseness of said retractable balls fitting in said annular groove may be eliminated.

* * * * *